United States Patent [19]

Dufresne et al.

[11] Patent Number: 5,283,256

[45] Date of Patent: Feb. 1, 1994

[54] CHOLESTEROL-LOWERING AGENTS

[75] Inventors: Claude Dufresne, East Brunswick, N.J.; Josep Guarro, Tarragona, Spain; Leeyuan Huang, Watchung, N.J.; Yu L. Kong, Edison, N.J.; Russell B. Lingham, Watchung, N.J.; Maria S. Meinz; Keith C. Silverman, both of Somerset, N.J.; Sheo B. Singh, Edison, N.J.

[73] Assignee: Merck & Co., Inc., Rahway, N.J.

[21] Appl. No.: 918,727

[22] Filed: Jul. 22, 1992

[51] Int. Cl.$^5$ .................. A61K 31/335; C07D 319/08
[52] U.S. Cl. ........................ 514/452; 549/363; 435/254.1
[58] Field of Search .................... 549/363; 514/452

[56] References Cited

U.S. PATENT DOCUMENTS

| | | | |
|---|---|---|---|
| 4,871,721 | 10/1989 | Biller et al. | 514/102 |
| 5,025,003 | 6/1991 | Biller et al. | 514/120 |
| 5,026,554 | 6/1991 | Bartizal et al. | 549/363 |
| 5,053,425 | 10/1991 | Bartizal et al. | 514/452 |
| 5,055,487 | 10/1991 | Bartizal et al. | 514/452 |
| 5,096,923 | 3/1992 | Bergstrom et al. | 514/452 |
| 5,102,907 | 7/1992 | Bergstrom et al. | 514/456 |
| 5,135,935 | 8/1992 | Alberts et al. | 514/305 |

FOREIGN PATENT DOCUMENTS

| | | |
|---|---|---|
| 0494622 | 7/1992 | European Pat. Off. . |
| 0450812 | 10/1991 | European Pat. Off. . |
| 0475706 | 3/1992 | European Pat. Off. . |
| 0409181 | 1/1991 | European Pat. Off. . |
| 0448393 | 9/1991 | European Pat. Off. . |
| WO92/12156 | 7/1992 | PCT Int'l Appl. . |
| WO92/12157 | 7/1992 | PCT Int'l Appl. . |
| WO92/12158 | 7/1992 | PCT Int'l Appl. . |
| WO92/12159 | 7/1992 | PCT Int'l Appl. . |
| WO92/12160 | 7/1992 | PCT Int'l Appl. . |

OTHER PUBLICATIONS

Biller et al., J. Med. Chem., 31: 1869–1871 (1988).
Poulter et al., J. Am. Chem. Soc., 111: 3734–3739 (1989).
Corey et al., J. Am. Chem. Soc., 98: 1291–1293 (1976).
Ortiz de Montellano et al., J. Med. Chem., 20: 243–249 (1977).
S. A. Biller et al., J. Med. Chem., 34: 1912 (1991).
S. A. Biller et al., J. Am. Chem. Soc., 113: 8522 (1991).
Oehlschlager et al., J. Org. Chem., 56: 3856 (1991).
Biller and Forster, Tetrahedron, 46: 6645 (1990).
Chen et al., Arch. Biochem. Biophys., 269: 544–547, Mar. 1989.
Hensens et al., J. Antibiotics, 45: 133–135 (1992).
Kobel and Traber, European Journal App. Microbiol. Biotechnol. 14: 237–240 (1982).
Baxter et al., J. Biol. Chem. 181, 267: 11705–11708 (1992).
Dawson et al., J. Antiobiotics 45: 639–647 (1992).
Sidebottom et al., J. Antibiotics 45: 648–658 (1992).

Primary Examiner—Nicky Chan
Attorney, Agent, or Firm—Catherine A. Dolan; Melvin Winokur; Paul D. Matukaitis

[57] ABSTRACT

This invention relates to compounds of structural formula (I):

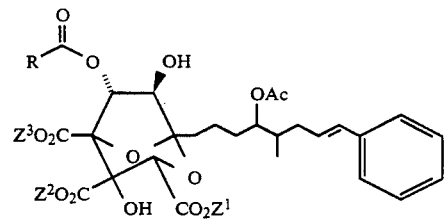

which are squalene synthase inhibitors and thus useful as cholesterol lowering agents and antifungal agents. These compounds are also inhibitors of farnesyl protein transferase and farnesylation of the oncogene protein Ras and thus useful in treating cancer. This invention also relates to a process for obtaining compounds of structural formula (I).

18 Claims, No Drawings

CHOLESTEROL-LOWERING AGENTS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin) and ZOCOR ® (simvastatin), now commercially available, are members of a group of very active antihypercholesterolemic agents that function by limiting cholesterol biosynthesis by inhibiting the enzyme HMG-CoA reductase.

Squalene synthase (also called squalene synthetase) is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analog containing compounds such as those described in P. Ortiz de Montellano et al., J. Med. Chem. 20, 243 (1977), E. J. Corey and R. Volante, J. Am. Chem. Soc., 98, 1291 (1976), and U.S. Pat. No. 5,025,003 to S. Biller. U.S. Pat. No. 4,871,721 to S. Biller describes isoprenoid(phosphinylmethyl) phosphonates as inhibitors of squalene synthase.

U.S. Pat. Nos. 5,096,923, 5,026,554; and 5,102,907 and 5,132,320 and U.S. patent application Ser. No. 698,766 filed May 10, 1991, now abandoned, disclose other non-phosphorus-containing substituted 2,8-dioxabicyclo[3.2.1]octane derivatives called Zaragozic Acids useful as squalene synthase inhibitors. Furthermore, J. Antibiotics 45: 639-658 (1992) reveals compounds called squalestatin.

Recently it has been shown that certain natural product nonphosphorous containing inhibitors of squalene synthase and their esters are useful in inhibiting fungal growth. This utility is described in U.S. Pat No. 5,026,554.

The present invention is directed to the use of semi-synthetic analogs of the above-noted natural products which are squalene synthase inhibitors for the inhibition of fungal growth.

The present invention is also directed to the use of compounds of formula I which inhibit farnesyl-protein transferase for inhibition of the oncogene protein Ras and treating cancer.

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., Microbiol. Rev. 53:171-286 (1989). Forms of Ras in cancer cells have mutations that distinquish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys—Aaa$^1$—Aaa$^2$—Xaa" box (Aaa is an aliphatic amino acid, the Xaa is any amino acid) (Willumsen et al., Nature 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., Proc. Natl. Acad. Sci. U.S.A. 86:8323 (1989)). In addition, Ha-Ras and N-Ras are palmitoylated via formation of a thioester on a Cys residue near a C-terminal Cys farnesyl acceptor (Gutierrez et al., EMBO J. 8:1093-1098 (1989); Hancock et al., Cell 57:1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., J. Biol. Chem. 263:18236 (1988); Farnsworth et al., J. Biol. Chem. 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62:81-88 (1990); Schaber et al., J. Biol. Chem., 265:14701-14704 (1990); Schafer et al., Science, 249:1133-1139 (1990); Manne et al., Proc. Natl. Acad. Sci. U.S.A., 87:7541-7545 (1990)).

Inhibition of farnesyl-protein transferase and, thereby, of farnesylation of the Ras protein, blocks the ability of Ras to transform normal cells to cancer cells. Surprisingly, the compounds of the invention inhibit Ras farnesylation and, thereby, generate soluble Ras which, as indicated infra can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., Proc. Natl. Acad. Sci, U.S.A. 86:6630-6634 (1989)). Cytosol-localized forms of Ras with normal GTPase activity do not act as inhibitors. Gibbs et al., ibid, showed this effect in Xenopus octyes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid: Reiss et. al., ibid; Reiss et al., *PNAS*, 88:732–736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras are described herein.

DETAILED DESCRIPTION OF THE INVENTION

The present invention is directed to novel compounds of structural formula (I) which are squalene synthase inhibitors:

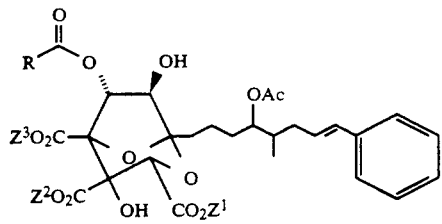

(I)

wherein

R is —(CH$_2$)$_n$CH$_3$ wherein n is 6 or 8; and

Z$^1$, Z$^2$ and Z$^3$ are independently:
a) H;
b) C$_{1-5}$alkyl; or
c) C$_{1-5}$alkyl substituted with
  i) phenyl, or
  ii) phenyl substituted with methyl, methoxy, halogen (Cl, Br, F, I) or hydroxy;

or a pharmaceutically acceptable salt of a compound of formula (I).

One subclass of compounds are those compounds in which n is 6. Exemplifying this subclass are those compounds wherein n is 6 and Z$^1$, Z$^2$ and Z$^3$ are each hydrogen or a pharmaceutically acceptable salt thereof. The compound wherein n is 6 and Z$^1$, Z$^2$ and Z$^3$ are each hydrogen is hereafter referred to as Zaragozic Acid D.

Further illustrating this subclass are those compounds in which n is 6 and in which one or more of Z$^1$, Z$^2$ or Z$^3$ is C$_{1-5}$ alkyl or C$_{1-5}$ alkyl substituted with phenyl or substituted phenyl wherein the substituent is methyl, methoxy, halogen or hydroxy.

Another subclass are those compounds in which n is 8 and Z$^1$, Z$^2$, and Z$^3$ are each hydrogen or a pharmaceutically acceptable salt thereof. The compound wherein n is 8 and Z$^1$, Z$^2$ and Z$^3$ are each hydrogen is hereafter referred to as Zaragozic Acid D2.

Further illustrating this subclass are those compounds in which n is 8 and in which one or more of Z$^1$, Z$^2$ or Z$^3$ is C$_{1-5}$ alkyl or C$_{1-5}$ alkyl substituted with phenyl or substituted phenyl wherein the substituent is methyl, methoxy, halogen or hydroxy.

The compounds of formula (I) are prepared in an aerobic fermentation procedure employing the fungal culture, MF5683, identified as *Amauroascus niger* or a mutant thereof. A mutant refers to an organism in which some gene on the genome is modified, leaving the gene or genes responsible for the organism's ability to produce the compounds of formula (I) in recoverable amounts functional and heritable. *Amauroascus niger* is an apparently rare organism. To our knowledge, less than five published accounts of this fungus exist. *Amauroascus niger* has only been isolated from dung of carnivores or by baiting the fungus from soil with hair.

The culture MF5683 is that of a fungus, *Amauroascus niger* Schroeter (Ascomycotina Onygenales), isolated from forest soil collected in Los Montes de Poblet, Tarragona, Spain. This isolate was recovered by using a technique commonly known as "hair baiting" whereby sterilized hair is incubated on the surface of moistened soil samples in petri dishes. Keratinophilic fungi preferentially colonize the hair. Fungal hyphae or spores are then transferred to a secondary isolation medium and purified. This culture has been deposited with the American Type Culture Collection at 12301 Parklawn Drive, Rockville, Md. 20852 as ATCC 74156 on May 27, 1992 under the conditions of the Budapest Treaty.

The culture MF5683, identified as *Amauroascus niger* exhibits the following morphological features.

Colonies attaining a diameter of 41 mm on MYE (1.0% malt extract, 0.2% yeast extract) agar after 14 days at 25° C., 50% relative humidity, 12 hr. photoperiod; aerial mycelium in discrete tufts 1–2 mm wide, pale cream-colored to light brown (Pale Ochraceous Buff, Pale Ochraceous Salmon, Light Buff) becoming darker brown with age. On potato-dextrose agar (Difco) 62 mm diameter after 14 days, aerial mycelium cottony, white with a very pale green tint (Light Viridine Green) in the center of the colony and with white or pale orange tinted margin (Orange Buff); reverse light orange (Orange buff, Capucine Yellow). Capitalized color names are from Ridgway, 1912, Color Standards and Color Nomenclature, Publ. by author, Washington, D.C.

Ascomata pulvinate, globose to subglobose 0.5–2.0 mm in diameter, white in color intially then becoming light to dark brown with age, consisting of a thin layer of undifferentiated hyphae surrounding a fertile centrum. Asci globose to ellipsoid, thin-walled, sometimes appearing slightly distended when ascospores mature, in clusters of 5 to 13 asci per ascoma, 10–12 μm in diameter, hyaline. Ascospores hyaline, globose, 4.5–5.0 μm in diameter, thick-walled, irregularly punctate-reticulate, 8 per ascus. Hyphae hyaline, septate, thin-walled, irregularly branched and anastamosing, 4.0–5.0 μm wide. Anamorphic state arthrosporic, with irregular hyaline arthroconidia, 6.5–11.0×4.0–5.0 μm.

The identification of *Amauroascus niger* was confirmed by comparison with the neotype strain of *Amauroascus niger* obtained from the American Type Culture Collection (ATCC 22339=Orr–0–315, isolated from soil from California). Both strains MF5683 and ATCC 22339 agree well with descriptions of *Amauroascus niger* published by Orr et al., 1966, Mycopathol. et Mycol. Appl. 25: 100–108, and Currah, 1985, Taxonomy of the Onygenales: Arthrodermataceae, Gymnoascacaeae, Myxotrichaceae and Onygenaceae. Mycotaxon 24: 1–216.

Compounds of this invention can be obtained by culturing the above-noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic conditions.

Compounds of formula (I) may be isolated from the aerobic fermentation of a culture of MF5683 (ATCC 74156). A culture of MF5683 (ATCC 74156) is defined as substantially free of its natural soil contaminants and free from deleterious viable contaminating microorganisms and capable of forming compounds of structural formula (I) in recoverable amounts. A biologically pure culture of MF5683 (ATCC 74156), that is, a culture free from any other viable microorganisms, may also be employed.

The fermentation procedure generally is to first inoculate a preserved source of culture into a nutrient seed medium and to obtain, sometimes through a two-step process, growth of the organisms which serve as seeds in the production of the active compounds After inoculation, the flasks are incubated with agitation at temperatures ranging from 20° to 30°C., preferably 25° to 28°C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 6 to 22 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

An alcoholic or oxygenated solvent, such as an ester or ketone, is employed to extract a compound of this invention from the solid fermentation medium. The preferred solvent for extraction of the solid fermentation is methyl ethyl ketone (MEK). The mixture of the solvent and fermentation broth is vigorously stirred and filtered. The resulting MEK layer is concentrated to dryness in vacuo for anion exchange chromatography and acetonitrile is added to dissolve the residue. The acetonitrile solution is sonicated and water is added to create an acetonitrile ($CH_3CN$):water solution, preferably 6:4 $CH_3CN$:$H_2O$, pH 4.5 to 6.5. The aqueous acetonitrile solution is loaded onto an ion exchange column, preferably BioRad AG4-X4 (formate cycle, pH 4.5) and the column is washed, preferably with 60 mM sodium formate in 6:4 $CH_3CN$:$H_2O$ pH 4.5. The preferred eluant is 0.2N sulfuric acid in 6:4 $CH_3CN$:$H_2O$. The eluant is extracted with ethyl acetate to yield the crude compound.

Further purification is accomplished using reversed-phase high pressure liquid chromatography (RP-HPLC). The preferred adsorbent for this chromatography is a octadecylsilane bonded phase silica gel. The preferred eluant for RP-HPLC is a mixture of acetonitrile and water buffered at low pH, such as 0.1% phosphoric or trifluoroacetic acid.

Esters of Zaragozic acids D and D2 may be prepared by dissolving Zaragozic acids D and D2 in a dry organic solvent, preferably tetrahydrofuran (THF) at 0°–30° C. and treating with the appropriately substituted isourea for 8–24 hours, cooling to −15° C. and filtering the urea (See Mathias, *Synthesis* 61–575 (1979)). The mono-, di- and tri- esters may be prepared by varying the number of equivalents of isourea used and can be selectively isolated by techniques such as HPLC or high speed countercurrent chromatography. The filtrate is concentrated under reduced pressure to yield the desired ester. Additionally, Zaragozic Acid D monomethylester has been isolated from the culture, possibly as an artifact of the isolation procedures.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

In addition, the present invention is directed to a method of inhibiting the enzyme squalene synthase which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form. These salts may be prepared by standard procedures.

The compounds of this invention may also be administered in combination with other cholesterol-lowering agents such as those which inhibit another enzyme in the biosynthetic pathway in the synthesis of cholesterol. Examples of such agents would include but are not limited to HMG-CoA reductase inhibitors, HMG-CoA synthase inhibitors, and squalene epoxidase inhibitors. Illustrative of such HMG-CoA reductase inhibitors are lovastatin, simvastatin, pravastatin and fluvastatin. Examples of HMG-CoA synthase inhibitors are the beta-lactone derivatives disclosed in U.S. Pat. Nos. 4,806,564; 4,816,477; 4,847,271; and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Illustrative examples of squalene expoxidase inhibitors are disclosed in European Patent Publication EP 0 318 860 and in Japanese Patent Publication J02169-571A. LDL-receptor give inducer molecules are disclosed in U.S. patent application Ser. No. 07/670,640 filed Mar. 18, 1991. Other cholesterol lowering agents that may be administered include niacin, probucol, and the fibric acids: clofibrate and gemfibrozil. Representative of such combinations are those containing about 10–400 mg of a compound of formula (I) in combination with about 20–100 mg of an HMG-CoA reductase inhibitor, or 20 to 200 mg, of a HMG-CoA synthase inhibitor, or 1 to 200 mg of a squalene epoxidase inhibitor, or 250–1000 mg of probucol, or 600–1200 mg of gemfibrozil, or 1–2 g of clofibrate, or 3–6 g of niacin, or 20–300 mg of an LDL-receptor gene inducer.

The compounds of this invention may also be co-administered with pharmaceutically acceptable non-toxic cationic polymers capable of binding bile acids in a non-resorbable form in the gastro-intestinal tract. Examples of such polymers include cholestyramine, colestipol and poly[methyl-(3-trimethyl)aminopropyl]imino-trimethylene dihalide. The relative amounts for co-administration of the compounds of this invention and these polymers is between 1:100 and 1:15,000 (w/w).

The intrinsic squalene synthase inhibitory activity of representative compounds of this invention was measured by the standard in vitro protocol described below:

PREPARATION OF HUMAN HepG2 Cell ENZYME

1. SOURCE: HEPG2 CELL LINE (Liver, hepatoblastoma, Human) ATCC No. HB 8065
2. CELL GROWTH AND MAINTENANCE Culture Medium: Minimum essential medium (MEM) with non-essential amino acids, sodium pyruvate, and 10% fetal bovine serum. The medium was changed twice weekly. A confluent monolayer was achieved in 1 week. The growth medium was prepared as listed below.

| Solution | (Volume ml) |
| --- | --- |
| 1. MEM (Gibco #320-1090AK) With Earle's salts and L-glutamine | 1000 |
| 2. Penicillin (10,000 units/mL), streptomycin (10,000 mg/mL), Gibco #600-5140 PG | 10 |
| 3. MEM sodium pyruvate, 10 mM (100X) Gibco #320-1140 | 10 |
| 4. MEM nonessential amino acids, 10 mM (100×) Gibco #320-1140AG | 10 |
| 5. L-glutamine, 200 mM (100×), Gibco #320-5030AG | 10 |
| 6. Hyclone fetal bovine serum, defined, Hyclone #A 111-L | 100 |

SUBCULTURE PROCEDURE: The medium was removed and washed with PBS (Phosphate-Buffered Saline 15.6 mM, pH 7.0). Fresh trypsin (0.25%)-EDTA (0.02%) with Hank's Balanced Salt solution was added and the flask was allowed to stand for a minute before the trypsin solution was removed. The flask was incubated at 37° C. until cells detached. Fresh medium was added and the cells were dispersed and dispensed into new flasks. Subcultivation ratio: 1:6.

PREPARATION OF DELIPIDATED SERUM: Fetal calf serum (100 ml) and CAB-O-SIL ™ (2 grams) were stirred overnight at 4° C. and centrifuged at 16,000 rpm for 5 hrs. The supernatant was filtered and the serum was stored at 4° C.

48 hrs. prior to harvest, cells grown in MEM with 10% Fetal Calf serum were switched to MEM with 10% delipidated serum.

HARVEST: The medium was removed and the cells were washed with PBS. Fresh trypsin (0.25%)-EDTA (0.02%) with Hanks' Balanced Salt solution was added and the cells allowed to stand for 1 min. and removed. The flask was incubated at 37° C. until the cells detached. MEM medium (6 mL/flask) was added to suspend cells and combined into a centrifuge tube. The cells were spun at 1,000 rpm for 5 mins. The cell pellet was resuspended in PBS and recentrifuged. Cells were counted ($2.5 \times 10^9$ yield from 18 flasks (75 cm$^2$)), and resuspended in 10 mL of 50mM HEPES (N-[2-Hydroxyethyl]piperazine-N'-[2-ethane sulfonic acid]) containing 5 mM MgCl$_2$, 2 mM MnCl$_2$, 10 mM DTT, pH 7.5 (enzyme suspension buffer).

CELL EXTRACTS: The cell suspension was sonicated (probe sonicator setting #60, pulse) on ice for 2 min. After a 1 min. cooling on ice, the sonication was repeated until greater than 90% of the cells were broken as observed microscopically. The cell suspension was centrifuged for 10 mins. at $12,000 \times g$ and the supernantant was transferred to a clean tube and centrifuged at $20,000 \times g$ for 20 mins The HepG2 enzyme preparation was centrifuged at $100,000 \times g$ to separate the cytosol and microsomal enzymes. The resulting pellet from the $100,000 \times g$ centrifugation, containing the squalene synthase, was resuspended in 5 mL of enzyme suspension buffer. The enzyme suspension was diluted and used to perform the squalene synthase assay using 3 $\mu$M $^3$H-farnesyl pyrophosphate as the substrate.

Preparation of Rat Liver Microsomes

Male, CHARLES RIVER CD rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA (ethylenediaminetetraacetic acid) pH 7.5 with a Potter-Elvehjem type tissue grinder. The homogenate was centrifuged twice at $20,000 \times g$ for 15 min. at 4° C., discarding the pellet each time. The supernatant was then centrifuged at $100,000 \times g$ for 1 hr at 4° C. The resulting microsomal pellet was resuspended in a volume of the above homogenizing buffer equal to one-fifth the volume of the original homogenate. This microsomal preparation has a protein concentration of about 5-6 mg/mL. The microsomal suspensions were stored in aliquots at $-70°$ C. squalene synthase activity in these aliquots is stable for a least several months.

Squalene Synthase Assay

Reactions were performed in 1.2 mL polypropylene tube strips of 8. Buffer mixture and substrate mixture for the assay were prepared from the following solution:

Buffer mixture contains 270 mM HEPES, pH 7.5, 20 mM Potassium fluoride and 5.4 mM Dithiothreitol (DTT). 55 $\mu$L of this mixture was used per assay. The final concentrations of HEPES, KF and DTT in the assay are 150 mM, 11 mM and 3 mM respectively.

| | Substrate mixture: | |
|---|---|---|
| Stock concentration | $\mu$L used per assay | Final concentration |
| 1. MgCl$_2$, 55 mM | 10 | 5.5 mM |
| 2. NADPH, 10 mM (made fresh) | 10 | 1 mM |
| 3. Squalene Epoxidase inhibitor, Banyu FW-439H, 0.5 mg per mL | 0.02 | 0.1 $\mu$g per mL |
| 4. $^3$H-farnesyl-pyrophosphate, 25 $\mu$M, 20 Ci per mole | 0.24 | 0.06 $\mu$M |
| 5. Farnesyl-pyrophosphate, 3 mM | 0.098 | 2.94 $\mu$M |
| 6. Water | 9.63 | |

For each reaction, 55 $\mu$L of buffer mixture was taken with 5 $\mu$L of an inhibitor solution in MeOH and 10 $\mu$L of diluted enzyme (the final protein concentration of enzyme in the assay is 1.2 $\mu$g per mL). The reaction was initiated by the addition of 30 $\mu$L of substrate solution and the mixture was incubated at 30° C. for 20 minutes. The reactions were stopped by the addition of 100 $\mu$L of 95% EtOH, vortexed, and 100 $\mu$L of a suspension of 1 gram per mL of BIO-RAD® AG 1×8 resin (400 mesh, Chloride form) was then added, vortexed. 800 $\mu$L of heptane was added to each tube strip and the strips were capped and vortexed for 10 minutes. 400 $\mu$L of heptane layer was then removed into a minivial and mixed with 2.5 mL of scintillation fluid and the radioactivity was determined by liquid scintillation counting. The controls were run with 5 $\mu$L of MeOH and blanks were run with the addition of 100 $\mu$L of 95% EtOH to denature the enzyme before the addition of the substrate mixture to the assay tube.

Percent inhibition is calculated by the formula:

$$\frac{(\text{Control} - \text{Sample})}{\text{Control} - \text{Blank}} \times 100$$

IC$_{50}$ values were determined by plotting the log of the concentration of the test compound versus the percentage inhibition. The IC$_{50}$ is the concentration of inhibitor that gives 50% inhibition as determined from these plots.

Below are IC$_{50}$'s representative of the inherent squalene synthase inhibitory activity of the compound of the present invention.

| SQUALENE SYNTHASE ACTIVITY | | |
|---|---|---|
| Compound | Human Enzyme IC$_{50}$ (nM) | Rat Liver Enzyme IC$_{50}$ (nM) |
| Zaragozic Acid D | 1 | 6 |
| Zaragozic Acid D2 | 2 | 6 |

The squalene synthase inhibitors are known to demonstrate broad spectrum antifungal activity as determined by broth dilution methods. The sensitivity of filamentous fungi and yeast is determined using inhibitor dilution assays in microtiter format. The compounds are dissolved in DMSO at 5 mg/mL and serially diluted by two-fold dilutions in 50 $\mu$L of sterile water. Exponential phase Candida, Cryptococus, Ustilago or other fungal or yeast cells are diluted in fresh liquid synthetic medium (Difco Yeast Nitrogen Base supplemented with 2% glucose (SM)) such that the inoculum was $1 \times 10^4$ cells/mL. Aspergillus spores are harvested from a well-sporulated Sabouraud Dextrose Agar slant in 0.4% Tween 80 and diluted into media to give an inoculum of $1 \times 10^3$ spores/mL. The wells are filled with 150 μL of inoculated media. The final drug concentration ranges from 50 to 0.078 μg/mL. The microtiter dishes are incubated at 29° C. for 20 to 48 hours. The minimum inhibitory concentration (MIC) is defined as the lowest concentration to prevent visible growth after incubation for 20 hours at 29° C. for the yeasts and 24 to 48 hours at 29° C. for the filamentous fungi.

Thus the present invention is also directed to a method of treating fungal infections which comprises the administration to an organism in need of such treatment a nontoxic therapeutically effective amount of a compound represented by the structural formula (I) and pharmaceutically acceptable salts thereof. Generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such as lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The compounds of formula (I) are also inhibitors of farnesyl transferase, as demonstrated below.

FARNESYL-TRANSFERASE ASSAY

I. PREPARATION OF SOLUTIONS REQUIRED FOR THE ASSAY i. 1.0M $MgCl_2$ (MW=203.3)

203.3 g $MgCl_2$ was dissolved in 1.0 L distilled water, and filtered through a sterile filter and stored at 4° C.

ii. 1.1M HEPES (MW=238.3) and 55.5 mM $MgCl_2$ 264.5 g of HEPES was added to 700 mL distilled water followed by 56 mL of 1.0M $MgCl_2$ The pH was adjusted to 7.5 with sodium hydroxide and the volume was brought to 1000 mL. The solution was filtered through a sterile filter and stored at 4° C.

iii. 0.5M Dithiothreitol (DTT, MW=154.24)

77.12 mg of DTT was dissolved in 1.0 mL of distilled water. A few drops of 10N NaOH was added to get the DTT to go into solution. 0.5M DTT was divided into 500 μL aliquots and stored at −20° C.

iv. Preparation of Assay Buffer (Prepare fresh daily)

100 μL of 0.5M DTT was added to 900 μL of 1.1M HEPES, pH 7.5 and 55.5 mM $MgCl_2$ to yield a 10X buffer consisting of 1.0M HEPES, pH 7.5, 50 mM $MgCl_2$ and 50 mM DTT.

v. Preparation of $^3$H-FPP

The $^3$H-FPP (NEN #NET-1042, MW=433.3) was used directly from the bottle as provided by NEN. The stock concentration of the $^3$H-FPP was 25 μM.

vi. Preparation of the reaction mix for Totals and unknown samples (on ice)

The reaction mix was prepared as below:

| Reagent | Stock Conc. | Vol to use/assay | Final Conc. in assay |
|---|---|---|---|
| $^3$H—FPP | 25 μM | 0.4 μL | 100 nM |
| ras-CVLS | 2.2 mg/mL (105 μM) | 0.619 μL | 0.65 μM |
| d-H$_2$O | | 18.98 μL | |
| TOTAL VOLUME | | 20 μL | |

A Blank reaction mix was also prepared with the negative control ras-protein, and the Total/Sample reaction mix received the ras-CVLS. The same volumes were used to prepare the Blank reaction mix as those in Table 1.

vii. Preparation of the farnesyl transferase solution

The farnesyl transferase solution was prepared as shown below. The farnesyl transferase mix was prepared right before use.

| Reagent | Stock Conc. | Vol to use/assay |
|---|---|---|
| d-H$_2$O | | 13.0 µL |
| Buffer | stock = 10× | 10.0 µL |
| F. Transferase | stock = 1.5 mg/mL | 2.0 µL |
| Total Volume | | 25 µL | viii. Preparation of 30% TCA Plus 10 mM Sodium Pyrophosphate

The stop solution was prepared by mixing 2.23 g sodium pyrophosphate with 350 mL water and 150 mL 100% TCA (trichloroacetic acid).

V. STEPS FOR THE ASSAY i. The assay volume was 100 µl, the volume of sample to be tested was 5 µl and the time of incubation is 60 min at room temperature.

ii. The TECAN 8000/505, an automatic pipetting station, added 50 µl of water plus 5 µl of sample to the assay tubes.

iii. The ras-CVLS reaction mix (20 µl) was manually added to totals and unknowns. The negative control ras-protein reaction mix (20 µL) was manually added to the blank tubes.

iv. The farnesyl transferase mix (25 µL) was manually added to all tubes to initiate the reaction and the assay tubes were kept at room temperature for 60 min.

v. The assay was stopped placing the assay tubes in an ice bath for 5 minutes.

vi. 100 µL of 30% TCA/H$_2$O plus 10 mM sodium pyrophosphate was then added to each tube. The assay tubes (uncapped) were incubated at 37° C. for 60 min to facilitate the hydrolysis of the FPP.

vii. Assay tubes were harvested through a TOMTEC 96-well harvestor (6×16 with extended tips, or SKATRON cell harvestor) onto LKB double thickness filter mats.

viii. The cell harvestor was adjusted so that each well was washed with 10 mL of 100% ethanol.

ix. Filter mats were baked in microwave oven for 6–8 min to dry the filtermats.

x. The filter mats were placed in counting bags, 30 mL of LKB β-scint cocktail was added and the filter mats were counted for 120 sec in the LKB β-plate counter

VI. RESULTS AND DISCUSSION

Percent inhibition was calculated according to the following equation:

$$\% \text{ Inhibition} = \frac{[\text{Total} - \text{Sample}]}{[\text{Total} - \text{Blank}]} \times 100$$

The Farnesyl transferase data presented below is a measurement of the ability of the test compound to inhibit Ras farnesylation in vitro

| Compound | IC$_{50}$ (nM) |
|---|---|
| Zaragozic Acid D | 100 |
| Zaragozic Acid D2 | 100 |

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone, or preferably, in combination with pharmaceutically-acceptable carriers or diluents, optionally with known-adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and-/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in a amount between about 0.1 mg/kg of body weight to about 20 mg/kg of body weight of a mammal per day, preferably of between 0.5 mg/kg of body weight to about 10 mg/kg of body weight of a mammal per day.

The following examples illustrate the preparation of the compounds of formula (I) and their incorporation into pharmaceutical compositions and, as such, are not to be considered as limiting the invention set forth in the claims appended hereto.

The composition of media employed in the following Examples are listed below:

| KFA SEED MEDIUM | | Trace Element Mix #2 | |
| --- | --- | --- | --- |
| | per liter | | g/L |
| Corn Steep Liquor | 5 g | FeSO$_4$.7H$_2$O | 1.0 |
| Tomato Paste | 40 g | MnSO$_4$.4H$_2$O | 1.0 |
| Oat Flour | 10 g | CuCl$_2$.2H$_2$O | 0.025 |
| Glucose | 10 g | CaCl$_2$.2H$_2$O | 0.1 |
| Trace Element | | H$_3$BO$_3$ | 0.056 |
| Mix | 10 mL | (NH$_4$)$_6$Mo$_7$O$_{24}$.4H$_2$O | 0.019 |
| Agar | 4 g | ZnSO$_4$.7H$_2$O | 0.2 |
| pH adjusted to 6.8 | | pH adjusted to 7.0 | |
| LSF1 Production Medium | | | |
| | per liter | | |
| Glycerol | 75 g | | |
| Dextrose | 10 g | | |
| Ardamine pH | 5 g | | |
| Soybean Meal | 5 g | | |
| Tomato Paste | 5 g | | |
| Sodium Citrate | 2 g | | |
| (NH$_4$)$_2$SO$_4$ | 2 g | pH adjustment = 7.0 | |

EXAMPLE 1

A. Culturing MF 5683

A 250 mL unbaffled Erlenmeyer flask with 54 mL of KFA medium was inoculated by transferring culture growth from the preserved culture in a soil tube using a sterile cotton swab which was prewetted with sterilized water. The flask was then incubated under aerobic conditions, at 25° C. for 3 days at 220 rpm and 85% relative humidity. This seeding culture was then used as an inoculum for production fermentation.

Thirteen flasks, each containing 45 mL of the production medium, LSF1, were each inoculated with two mL of the above seeding culture. Flasks were then incubated at 25° C. at 220 rpm and 85% relative humidity for 7 days. Cultures were then pooled together. 250 mL of pooled cultures were then used for further extraction and isolation. The broth was frozen for storage.

B. Isolation of Zaragozic Acids D and D2

The frozen broth (250 mL) was thawed and extracted with methyl ethyl ketone (MEK) (250 mL). The MEK extract was evaporated to dryness, and acetonitrile (30 mL) was added to the residue. After sonication, the acetonitrile solution was diluted with water (20 mL, pH 6.5). The aqueous acetonitrile solution was then loaded onto an ion exchange column (5 mL resin bed; BIORAD ® AG4-X4; formate cycle; pH 4.5) with a flow rate of ca. 0.5 mL/min. The column was then washed with 25 mL of 60 mM sodium formate in 60:40 acetonitrile/water (pH 4.5). (The sodium formate solution is prepared as follows: A 2N formic acid solution in water is adjusted to pH 3 with NaOH. A 30 mL aliquot is then added to 370 mL of water, followed by dilution with 600 mL acetonitrile. The resulting solution then has an apparent pH of 4.5.) The column was subsequently eluted with 25 mL of 0.2N sulfuric acid in 60:40 acetonitrile/water. The eluate was diluted with ethyl acetate (50 mL) and the aqueous layer discarded. The organic layer was washed with water (5 mL), and then evaporated to dryness on the rotovap. The residue was dissolved in methanol (250 ul) and injected on a semi-preparative HPLC column. Using a DYNAMAX ® 60 A, C8 column (8 um; 10×250 mm with guard column) eluting at 4 mL/min (65% acetonitrile/35% 0.1% phosphoric acid in water; pH 2.5), fractions were collected at 1.0 min intervals. Three main peaks were observed. The corresponding fractions (Fractions 10–12, 15–16, and 17–20) were combined and extracted with an equal volume of ethyl acetate. The ethyl acetate layer was then evaporated to dryness. NMR spectra were then obtained for each one. Fractions 10–12 contained Zaragozic Acid D. Fractions 15–16 contained Zaragozic Acid D C3-monomethyl ester, likely produced as an artifact of isolation. Fractions 17–20 contained Zaragozic Acid D2.

EXAMPLE 2

Preparation of an Ammonium Salt

A 0.1 mmol sample of the free acid of a compound of formula (I) is dissolved in 10 mL ethyl acetate. The resulting solution is saturated with gaseous ammonia and the ammonium salt precipitates from solution.

EXAMPLE 3

Preparation of a Potassium Salt

A solution of 0.1 mmol of the free acid of a compound of formula (I) in 10 mL methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts can be formed.

EXAMPLE 4

Preparation of a Calcium Salt

A solution of 0.1 mmol of the free acid of a compound of formula (I) in 20 mL 6:4 methanol:water is treated with an aqueous solution of 0.1 mmol of calcium hydroxide. The solvents are evaporated to give the corresponding calcium salt.

EXAMPLE 5

A solution of 0.1 mmol of the free acid of a compound of formula (I) in 10 mL of methanol is treated with 0.1 mmol of ethylenediamine. Evaporation of the solvent affords the ethylenediamine salt. The procedure can also be applied to the preparation of the N,N''-dibenzylethylenediamine salt.

EXAMPLE 6

Preparation of a Tris(hydroxymethyl)aminomethane Salt

To a solution of 0.1 mmol of the free acid of a compound of formula (I) in 10 mL of methanol is added from 0.1 to 0.3 mmol of tris(hydroxy-methyl)aminomethane dissolved in 10 mL of methanol. Evaporation of the solvent gives a corresponding salt form, the exact composition of which is determined by the molar ratio of amine added. Similarly prepared are the salts of L-ornithine, L-lysine, and N-methylgluatamine.

EXAMPLE 7

Preparation of an L arginine Salt

A solution of 0.1 mmol of the free acid of a compound of formula (I) in 20 mL of 6:4 methanol: water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglutamine.

EXAMPLE 8

Preparation of A Tri-Methyl Ester of A Compound of Formula (I)(Method 1)

The free acid of a compound of formula (I) (0.6 mg) is dissolved in 1 mL diethyl ether and stirred at 0° C. Etheral cyanamide is added dropwise until the solution remains yellow. The solution is evaporated under a stream of nitrogen to yield the corresponding trimethyl ester.

EXAMPLE 9

Preparation of A Tri-Methyl Ester of A compound of Formula (I)(Method 2)

To 5 mg of the free acid of a compound of formula (I) in methanol (5 mL) is added 2 mL of freshly distilled diazomethane in ether (2.05M). After 5 minutes the solvent is removed to afford the corresponding tri-methyl ester as an oil.

EXAMPLE 10

Preparation of A Tri-Methyl Ester of A Compound of Formula (I) (Method 3)

A solution of 5 mg of the free acid of a compound of formula (I) in 0.5 mL of tetrahydrofuran (THF) is treated at room temperature with 3 equivalents of N,N'-diisopropyl-O-benzyl isourea for 18 hours. The reaction mixture is then chilled to −15° C., filtered to remove the urea. The filtrate is concentrated under reduced pressure to yield the corresponding tri-methyl ester. The method of Example 10 is also suitable for the preparation of other ester derivatives such as: 1) methyl and the other lower alkyls, and 2) substituted benzyl esters, using the appropriately substituted isourea. By varying the number of equivalents of the substituted isourea used, the mono-, di- and tri-substituted esters may be selectively prepared.

EXAMPLE 11

Oral Composition

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

Mass Spectral Data

Mass spectra were recorded on Finnigan-MAT model MAT212 (Electron Impact, EI, 90 eV) and TSQ70B (Fast Atom Bombardment, FAB) mass spectrometers. Exact mass measurements were performed at high resolution (HR-EI) using perfluorokerosene (PFK) as internal standard. FAB mode used as matrices 5:1 dithiothreitol/dithioerythritol (DTT/DTE, negative ion mode) DTT/DTE doped with lithium acetate, and thioglycerol doped with acetic acid (positive ion mode).

$^{13}C$ NMR Data $^{13}C$ NMR spectra were recorded in $CD_3OD$ at 75 MHz on a Varian XL-300 spectrometer. Chemical shifts are given in ppm relative to the solvent peak at 49.0 ppm ($CD_3OD$) as internal standard.

$^1H$ NMR Spectra $^1H$ NMR spectra were recorded at 500 MHz on a Varian Unity 500. Chemical shifts are shown in ppm relative to the solvent peaks at 3.30 ppm ($CD_3OD$) as internal standards.

Physical Properties of the compounds of Structure I: Zaragozic Acid D—the compound of structure (I) wherein n is 6 and $Z^1$, $Z^2$ and $Z^3$ are each hydrogen.

Mass Spectral Data:

This compound has the molecular weight of 678.2904 by HRMS.

$^1H$ NMR (500 MHz in $CD_3OD$) δ 0.88 (t, 7.0, 3H), 0.94 (d, 7.0, 3H), 1.3 (m, 8H), 1.59 (m, 4H), 1.69 (m, 2H), 1.89 (m), 1.92 (m, 2H), 2.05 (s, $^3H$), 2.08 (m), 2.28 (m, 2H), 2.32 (m), 4.02 (d, 2.0), 4.95 (m), 5.23 (s), 6.23 (dt, 16.0, 7.0), 6.24 (d, 2.0), 6.38 (d, 16.0), 7.15 (br t, 7.5), 7.25 (t, 7.5, 2H), 7.34 (br d, 7.5, 2H).

$^{13}C$ NMR (75 MHz in $CD_3OD$) δ 14.44, 14.64, 20.12, 21.16, 23.70, 25.86, 30.07, 30.15, 32.68, 32.86, 35.04, 36.31, 37.97, 38.02, 75 67, 76.63, 78.03, 80.99, 82.20, 90.97, 107.21, 127.04 (2), 127.95, 129.51 (2), 129.61, 132.87, 139.12, 168.48, 170.22, 172.52, 173.08, 173.64.

Zaragozic Acid D2—the compound of structure (I) wherein n is 8 and $Z^1$, $Z^2$ and $Z^3$ are each hydrogen.

Mass Spectral Data:

This compound has the molecular weight of 706.3194 by HRMS.

The $^1H$ NMR spectrum is nearly identical to that for Zaragozic Acid D. The only change is the larger integral area for the protons at 1.3 ppm, suggesting 2 additional methylene groups.

The $^{13}C$ NMR is also nearly identical to that of Zaragozic Acid D with the exception of two additional resonances in the 30.0–30.5 ppm range.

Zaragozic Acid D C3-monomethyl ester—The compound of structure (I) wherein n is 6, $Z^1$ is methyl and $Z^2$ and $Z^3$ are each hydrogen.

The $^1H$ NMR Spectrum is nearly identical to that of Zaragozic Acid D except for an additional $^3H$ singlet at 3.70 ppm.

What is claimed is:

1. A compound of structural formula (I)

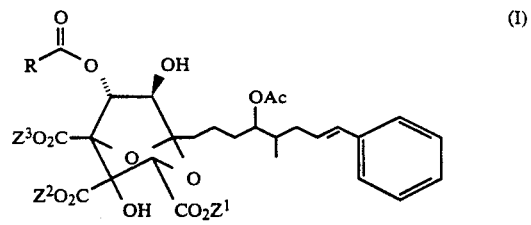

(I)

wherein R is —$(CH_2)_nCH_3$ wherein n is 6 or 8; and $Z^1$, $Z^2$ and $Z^3$ are each independently
   a) H;
   b) $C_{1-5}$ alkyl; or
   c) $C_{1-5}$ alkyl substituted with
      i) phenyl, or
      ii) phenyl substituted with methyl, or a pharmaceutically acceptable salt of a compound of formula (I).

2. A compound of molecular weight 678.290 characterized by:
   (a) the $^{13}C$ NMR chemical shifts as measured in $CD_3OD$: δ 14.44, 14.64, 20.12, 21.16, 23.70, 25.86, 30.07, 30.15, 32.68, 32.86, 35.04, 36.31, 37.97, 38.02, 75.67, 76.63, 78.03, 80.99, 82.20, 90.97, 107.21, 127.04 (2), 127.95, 129.51 (2), 129.61, 132.87, 138.12, 168.48, 170.22, 172.52, 173.08, 173.64, and (b) the $^1$H NMR chemical shifts as measured in CD$_3$OH: δ 0.88 (t, 7.0, 3H), 0.94 (d, 7.0, 3H), 1.3 (m, 8H), 1.59 (m, 4H), 1.69 (m, 2H), 1.89 (m), 1.92 (m, 2H), 2.05 (s, 3H), 2.08 (m), 2.28 (m, 2H), 2.32 (m), 4.02 (d, 2.0), 4.95 (m), 5.23 (s), 6.23 (dt, 16.0, 7.0), 6.24 (d, 2.0), 6.38 (d, 16.0), 7.15 (br t, 7.5), 7.25 (t, 7.5, 2H), 7.34 (br d, 7.5, 2H).

3. The compound of claim 1 in which $Z^1$, $Z^2$ and $Z^3$ are each hydrogen or a pharmaceutically acceptable mono, di or tri salt thereof.

4. The compound of claim 1 in which $Z^1$, $Z^2$ and $Z^3$ are each methyl.

5. The compound of claim 3 in which n is 6.

6. The compound of claim 3 in which n is 8.

7. A pharmaceutical composition comprising a nontoxic therapeutically effective amount of a compound of claim 1 and a pharmaceutically acceptable carrier.

8. A pharmaceutical composition comprising a nontoxic therapeutically effective amount of a compound of claim 1 in combination with a pharmaceutically acceptable non-toxic cationic polymer capable of binding bile acids in a non-resorbable form in the gastrointestinal tract and a pharmaceutically acceptable carrier.

9. A pharmaceutical composition comprising a nontoxic therapeutically effective amount of a compound of claim 1 in combination with a nontoxic therapeutically effective amount of a cholesterol lowering agent selected from the group consisting of:
   a) HMG-CoA reductase inhibitor;
   b) HMG-CoA synthase inhibitor;
   c) squalene epoxidase inhibitor;
   d) probucol;
   e) niacin;
   f) gemfibrozil;
   g) clofibrate; and
   h) LDL-receptor gene inducer.

10. A pharmaceutical composition comprising a unit dose of a compound of claim 1 and a nontoxic therapeutically effective amount of an HMG-CoA reductase inhibitor.

11. A method of treating hypercholesterolemia comprising the administration to a subject in need of such treatment a nontoxic therapeutically effective amount of a compound of claim 1.

12. A method of inhibiting squalene synthase comprising the administration to a subject in need of such treatment a nontoxic therapeutically effective amount of a compound of claim 1.

13. A method of treating hypercholesterolemia comprising the administration to a subject in need of such treatment 20 to 100 mg of a compound of claim 1.

14. A method of inhibiting squalene synthase comprising the administration to a subject in need of such treatment 20 to 100 mg of a compound of claim 1.

15. A method for inhibiting fungal growth comprising applying to the area where growth is to be controlled an antifungally effective amount of a compound of claim 1.

16. A method for inhibiting fungal growth in a living organism in need of such treatment comprising the oral, systemic, topical or parenteral administration to the living organism of an antifungally effective amount of a compound of claim 1.

17. The method of claim 16 wherein the living organism is a vertebrate.

18. The method of claim 16 wherein the living organism is a plant, and the compound is administered by topical application to the plant or to the soil in which the plant grows.

* * * * *